United States Patent
Hamasaki et al.

(10) Patent No.: US 9,964,539 B2
(45) Date of Patent: May 8, 2018

(54) ANALYSIS DEVICE AND ANALYSIS METHOD

(71) Applicant: Hitachi High-Technologies Corporation, Tokyo (JP)

(72) Inventors: Koshin Hamasaki, Tokyo (JP); Toshiro Saito, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days. days.

(21) Appl. No.: 14/412,949

(22) PCT Filed: Jun. 12, 2013

(86) PCT No.: PCT/JP2013/066143
§ 371 (c)(1),
(2) Date: Jan. 5, 2015

(87) PCT Pub. No.: WO2014/007034
PCT Pub. Date: Jan. 9, 2014

(65) Prior Publication Data
US 2015/0153335 A1  Jun. 4, 2015

(30) Foreign Application Priority Data
Jul. 6, 2012 (JP) ................................. 2012-151993

(51) Int. Cl.
*G01N 33/543* (2006.01)
*G01N 21/64* (2006.01)
*C12Q 1/68* (2018.01)

(52) U.S. Cl.
CPC ..... *G01N 33/54333* (2013.01); *C12Q 1/6834* (2013.01); *G01N 21/6428* (2013.01);
(Continued)

(58) Field of Classification Search
None
See application file for complete search history.

(56) References Cited

U.S. PATENT DOCUMENTS

| 5,705,402 A | 1/1998 | Leland et al. |
| 2003/0073086 A1 | 4/2003 | Guire et al. |

(Continued)

FOREIGN PATENT DOCUMENTS

| EP | 2765424 A1 | 8/2014 |
| JP | 6-508203 A | 9/1994 |

(Continued)

OTHER PUBLICATIONS

Liu et al., Using Azobenzene-Embedded Self-Assembled Monolayers to Photochemically Control Cell Adhesion Reversibly, 2009, vol. 49, pp. 4406-4408.*

(Continued)

*Primary Examiner* — Neil N Turk
(74) *Attorney, Agent, or Firm* — Mattingly & Malur, PC

(57) ABSTRACT

Biomolecules are specifically captured with magnetic particles and the biomolecules are labeled with fluorescence. A magnetic field generator, for attracting the magnetic particles to the support substrate, is provided on the reverse face of the support substrate, and an adhesion layer is provided on the surface of the support substrate to hold the magnetic particles. First, a dispersing solution for the magnetic particles is placed on the surface of the support substrate with the magnetic field in an off state. Next, the magnetic field is turned on, and the magnetic particles in solution are attracted to the support substrate surface. The magnetic particles colliding with the support substrate adhere to the adhesion layer of the support substrate surface, and then the magnetic field is turned off. Thus, aggregations can be broken up while the magnetic particles are held, and a magnetic particle layer on the support substrate can be a single layer.

20 Claims, 8 Drawing Sheets

(52) U.S. Cl.
CPC ..... *G01N 21/6458* (2013.01); *G01N 21/6489* (2013.01); *G01N 33/54326* (2013.01); *G01N 33/54346* (2013.01); *G01N 2021/6441* (2013.01)

(56) References Cited

U.S. PATENT DOCUMENTS

| | | | |
|---|---|---|---|
| 2003/0127609 A1* | 7/2003 | El-Hage et al. | 250/574 |
| 2004/0005718 A1 | 1/2004 | Fukushima | |
| 2004/0234898 A1* | 11/2004 | Batishko et al. | 430/312 |
| 2005/0239216 A1* | 10/2005 | Feistel | 436/526 |
| 2006/0281104 A1* | 12/2006 | MacEvicz | G01N 33/582 435/6.11 |
| 2007/0290683 A1* | 12/2007 | Ikeda et al. | 324/260 |
| 2009/0111094 A1* | 4/2009 | Storhoff | G01N 33/54386 435/6.11 |
| 2009/0321662 A1 | 12/2009 | Ohtsuka | |
| 2011/0065209 A1 | 3/2011 | Heil et al. | |
| 2013/0053280 A1 | 2/2013 | Hamasaki et al. | |

FOREIGN PATENT DOCUMENTS

| | | |
|---|---|---|
| JP | 07-248330 A | 9/1995 |
| JP | 2003-523185 A | 8/2003 |
| JP | 2004-333168 A | 11/2004 |
| JP | 2010-8247 A | 1/2010 |
| WO | 01-51668 A1 | 7/2001 |
| WO | 2005/093416 A1 | 10/2005 |
| WO | 2011/142307 A1 | 11/2011 |
| WO | 2013-051651 A1 | 4/2013 |

OTHER PUBLICATIONS

David M. Rissin et al., Single-Molecule Enzyme-Linked Immunosorbent Assay Detects Serum Proteins at Subfemtomolar Concentrations, NIH Public Access, Author Manuscript, Nat Biotechnol, Jun. 2010, 28(6): 595-599.

Extended European Search Report received in corresponding European Application No. 13812577.8 dated Jan. 8, 2016.

\* cited by examiner

ANALYSIS DEVICE AND ANALYSIS METHOD

TECHNICAL FIELD

The present invention relates to a biomolecule analysis method using magnetic particulates and a biomolecule analyzer.

BACKGROUND ART

In recent years, in the field of cancer diagnosis, various cancer markers have been investigated in order to know a sign of cancer onset in an early stage, and practical applications is progressing. The cancer marker is a secretory biological factor derived from cancer cells, and increases with the progression of the cancer and appears in blood and/or urine. For example, proteins such as hormones and cytokines, and nucleic acid such as micro-RNA are known. In the early stage cancer, the amount of these cancer markers is small and difficult to detect these markers; it is the same situation when there exists the cancer marker of originally low expression level. At present, the mainstream of the high sensitive method for detecting the cancer markers is in the immunoassay method using an antibody, and the techniques such as the ELISA method and the nanoparticulate assay are known. Recently, although it is still in a study stage, as a further high sensitive immunoassay method, a digital ELISA which is capable of detecting by a single molecule has been developed (Non-Patent Literature 1). When the cancer marker in blood is detected, the amount of blood which can be collected from patient is limited; therefore, it is required to detect by capturing a trace amount of the cancer marker contained therein as much as possible. For example, if the detection is performed with 50 μl of plasma, since the cancer marker in the early stage cancer is within the concentration range from $10^{-16}$ to $10^{-12}$ M, the detection sensitivity which can determine quantitatively 3000 molecules of the target molecule present in 50 μl of the plasma is necessary. Thus, detection device with very high sensitivity which is capable of detecting the cancer markers of low concentrations is required.

CITATION LIST

Non Patent Literature

Non-Patent Literature 1: Rissin D M et al., Nature Biotechnology, June 28(6); p 595-599 (2010)

SUMMARY OF INVENTION

Technical Problem

In order to determine quantitatively a trace amount of biomolecules, the biomolecules are captured specifically with magnetic particulates, and the biomolecules are labeled with fluorescence. The detection is performed by immobilizing the biomolecules captured on the magnetic particulates to a supporting substrate. The magnetic particulates capturing the biomolecules suspending in a liquid are attracted to the surface of the supporting substrate by a magnetic field. Since the magnetic particulates themselves are magnetized in the presence of a magnetic field, the particulates pull each other on the surface of the supporting substrate and, therefore, the magnetic particulates aggregate. When the magnetic particulates aggregate, the magnetic particulates would overlap in the direction perpendicular to the surface of a plate on the support base. In addition, the aggregated particulates would enfold the fluorescent labels internally.

There is a problem that the magnetic particulates overlapped in this way or the magnetic particulates enfolding fluorescent labels internally will not be counted accurately at the time of fluorescence observation.

Solution to Problem

In order to attract the magnetic particulates to the supporting substrate, a magnetic field generator, which can switch on/off, on the back surface of the supporting substrate and an adhesive layer, which holds the magnetic particulates, on the front surface of the supporting substrate are provided. First, a dispersed solution of the magnetic particulates is placed on the front surface of the supporting substrate with the magnetic field of the front surface of the supporting substrate being off. Next, the magnetic field is turned on and the magnetic particulates in the solution are attracted onto the front surface of the supporting substrate. The magnetic particulates collided onto the supporting substrate are forced to adhere to the adhesion layer of the front surface of the supporting substrate and, further, the magnetic field is turned off.

Advantageous Effects of Invention

According to the present invention, the majority of magnetic particulates in the liquid can be attracted to the surface of the support base, and held by the adhesive layer. Further, by turning off the magnetic field, the aggregation among the magnetic particulates can be resolved, and the magnetic particulate layer on the supporting substrate can be made single-layered. By making the magnetic particulate layer single-layered, focusing to the fluorescent dyes on the support base can be performed easily, and by preventing the engulfment of fluorescent dyes due to the aggregation of the magnetic particulates, quantitativity is improved. Since the capture rate of biomolecules, which are the analysis object, can be improved significantly by the biomolecule analysis using the present invention, detection with higher sensitivity than in the prior art is possible. Further, because the device having a complex structure is not required, it is very simple in comparison with the prior art and a significant improvement of throughput can be obtained by combining with the automatic control unit.

DESCRIPTION OF EMBODIMENTS

Figure 1:
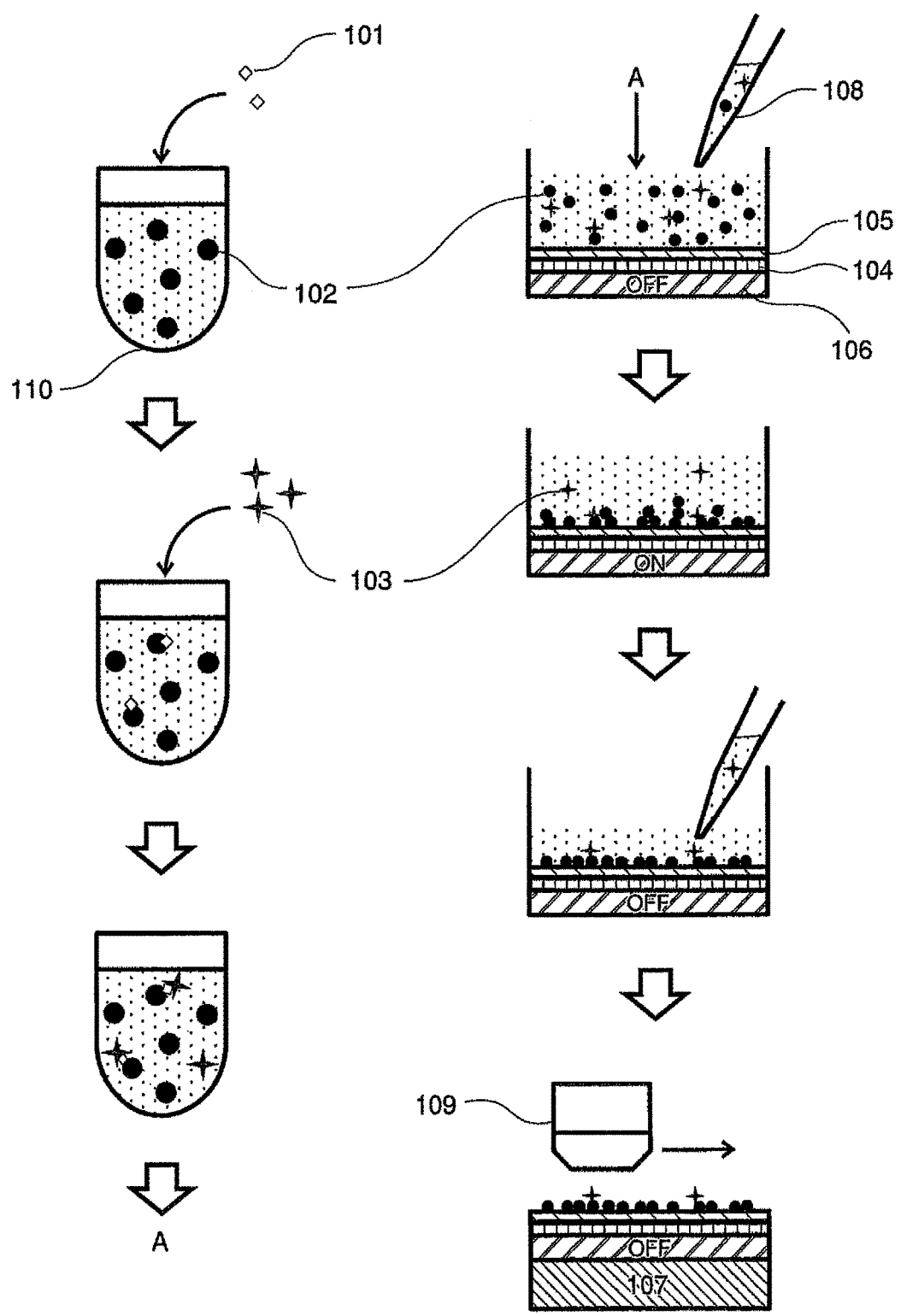
FIG. 1 is a figure for explaining one example of the analysis method of the present example.

In the nucleic acid analysis device according to one example of the present invention, biomolecules of the analysis object are captured by magnetic particulates, a device has a smooth supporting substrate for presenting the particulates two-dimensionally, and there exists an adhesive layer for immobilizing the magnetic particulates with antibodies onto the surface of the supporting substrate. As a supporting substrate, a thin quartz glass substrate or a silicon substrate which transmits the magnetic force well is suitable, and according to the type of the adhesive layer, a quartz glass substrate or a silicon substrate deposited with a metal thin film may be used properly. The adhesive surface for immobilizing the magnetic particulates modified with protein is a hydrophobic adhesive layer or a biotin-introduced adhesive layer and, as a hydrophobic adhesive agent, a self-assembled film of alkyl group is used. In addition, here is disclosed use of photoresponsive azobenzene as adhesive which can switch reversibly the strength of adhesive force of the adhesive layer. As to a functional group used for immobilizing to the supporting substrate, a silanol group is used if the substrate is quartz or an oxidation-treated silicon substrate; a thiol group is used if the substrate is a gold-deposited substrate; and a phosphate group is used if the substrate is a titanium-oxide-deposited substrate. A magnetic field generator for attracting the magnetic particulates with biomolecules to the adhesive layer is installed just beneath the supporting substrate and, furthermore, the magnetic field generator is equipped with a function of switching on/off or the intensity levels of the magnetic field. The magnetic field generator is selected from an electromagnet, a movable permanent magnet, a movable electromagnet, and a permanent magnet or an electromagnet equipped with a movable magnetic field shielding plate between the supporting substrate and the magnet. The present device is used while installing the supporting substrate on a movable stage so that fluorescence observation can be performed by scanning the entire surface of the supporting substrate with an imaging device fixed.

An observation procedure will be explained. At the beginning, a reaction solution containing the magnetic particulates capturing the objective biomolecules is placed on the supporting substrate, a magnetic field is generated next by turning on the magnetic field generator so that all magnetic particulates in the reaction solution are attracted on the support base, and the magnetic particulates contacting with the adhesive layer are immobilized to the supporting substrate. The magnetic particulates which did not contact with the adhesive layer for the first time are increased in collision opportunities of the magnetic particulates with the adhesive layer by repeating the on/off or up-and-down of the magnetic field. After immobilizing the magnetic particulates to the adhesive layer, suspending unreacted fluorescence-labeled antibodies are rinsed away by flushing a cleaning solution. A photograph is taken while irradiating the excitation light to the magnetic particulates immobilized on the supporting substrate and to the fluorescence-labeled antigen bound thereto. By counting the number of observed bright spots, the concentration of the objective biomolecules is determined.

As for the observation procedure using a device having a function of changing reversibly the adhesive force of the adhesive layer, on the occasion of immobilizing the magnetic particulates, while azobenzene is changed to a cis-form by irradiation of ultraviolet light, a certain amount of the reaction solution is poured under the state where the magnetic field is turned off. After that, the magnetic particulates in the reaction solution are attracted onto the support base by generating a magnetic field, and the magnetic particulates contacting with the adhesive layer are immobilized on the supporting substrate. After immobilizing the magnetic particulates to the adhesive layer, floating unreacted fluorescence-labeled antibodies are rinsed away by flushing a cleaning solution. A photograph is taken while irradiating the excitation light to the magnetic particulates immobilized on the supporting substrate and to the fluorescence-labeled antigen bound thereto, and the concentration of the objective biomolecules is determined by counting the number of observed bright spots. After completion of observation, by applying visible light or heat to the supporting substrate, azobenzene is made hydrophilic, and the magnetic particulates are peeled off from the supporting substrate. Irradiation of ultraviolet light and visible light is configured to be able to be implemented on the entire surface of the supporting substrate by preparing light sources and a wavelength separation filter aside from the detection system. As a method for applying the heat, heated hot water is passed through a flow path. When cleaning has completed, by returning to the cis-form again by irradiation of ultraviolet light, immobilization and observation are carried out in the same way by pouring a new sample. In order to reduce the drag-in of the sample at the second run or later, repeated washing is performed. Otherwise, the contamination is removed by changing the wavelength of the fluorescent dye and the detection filter used for labeling in each time of the measurement.

In the Examples, it is disclosed that the biomolecules of the analysis object are peptides, proteins, or a group of nucleic acid fragments. A method of immunological analysis which is characterized in that antigens of the analysis object are prepared, the magnetic particulates bound to antibodies against the antigens and the phosphor-labeled antibodies are coupled with the antigens of the analysis object, and the labeling phosphors are detected, will be disclosed. Alternatively, a nucleic acid analysis method characterized in that the nucleic acid fragment group of the analysis object is prepared, nucleic acid molecules which have known nucleotide sequences and labeled with phosphors are hybridized with the nucleic acid fragment group of the analysis object, and the phosphors labeled on the hybridized nucleic acid molecules are detected will be disclosed.

In addition, in an Example, a nucleic acid analysis method which is characterized in that, in the biomolecule analysis method, the phosphor labels are the particulates containing plural kinds of phosphors with different mixing ratios for each type of biomolecules of the analysis object will be disclosed. In addition, in an Example, a biomolecule analysis method which is characterized in that, in the biomolecule analysis method, by using the same phosphor label for the molecular species other than specific molecular species, counting the number of fluorescent bright spots for each molecule, and calculating a ratio of the number of bright spots of each specific molecular species to the total number of bright spots, the abundance of the each specific molecular species is evaluated, will be disclosed. In addition, in an Example, a biomolecule analysis method which is characterized in that, in the nucleic acid analysis method, a step of labeling a biomolecule group of the analysis object with a common phosphor and subjecting biomolecules labeled with a phosphor having different fluorescence wavelength or fluorescence intensity from the phosphor to binding reaction specifically is included, and by calculating a ratio between the numbers of bright spots of the former and the latter phosphor, the abundance of each type of biomolecules of the analysis object is evaluated, will be disclosed.

In addition, in an Example, a biomolecule analyzer characterized by including a device for immobilizing biomolecules of the analysis object as deploying two-dimensionally, a biomolecule analyzer installed with the device, and a means for measuring the fluorescence of the phosphor, will be disclosed.

Hereinafter, the above-described and the other novel features and effects of the present invention will be explained with reference to the figures. Here, for thorough understandings of the present invention, detailed descriptions are made on specific embodiments; however, the present invention is not limited to the contents described herein.

Example 1

One example of the analysis method and the configuration of the device of the present Example are explained with reference to FIG. 1. In the beginning, biomolecules to be detected are captured by magnetic particulates in advance, and further labeled with fluorescent labels. All of these reactions are carried out under a normal temperature in a buffer solution, and either one of the reaction of magnetic particulates with biomolecules and the reaction of fluorescence labelling substances with biomolecules may be carried out first, or may be carried out at the same time. The preparation method of magnetic particulates to capture and the method of fluorescence labeling will be described in detail in Examples 3 and 4.

In the present Example, the reaction method is explained with reference to FIG. 1 by taking as an example a method that the biomolecules to be detected are antigens 101, antigens 101 are captured by antibody-bound magnetic particulates 102, and further they are labeled with fluorescence-labeled antibodies 103. First, the antibody-bound magnetic particulates 102 are placed in a reaction vessel 110, and stirred well. To this solution, a solution containing the antigens 101 to be detected is added and mixed well, and incubated for a few minutes. At this time, the reaction is accelerated by either rotating the reaction vessel up and down or by agitating with shaking. As to the ratio of mixing, the antibody-bound magnetic particulates 102 are mixed so as to be excessive as compared with the antigens 101. Further, to this reaction solution, the fluorescence-labeled antibodies 103 are added, and incubated for an additional few minutes. In the mixed solution thus reacted, a large amount of unreacted magnetic particulates 102 and fluorescence-labeled antibodies 103 are present, and a small amount of a mixture of magnetic particulates 102 and antigens 101 and fluorescence-labeled antibodies 103 are present therein. Hereinafter, this mixed solution is referred to as a reaction solution A. The reaction solution A is deployed two-dimensionally on the supporting substrate, and the amount of antigens is determined by detecting the fluorescence.

Next, a configuration of a device for detection of fluorescence is explained with reference to FIG. 1. The present device has a smooth supporting substrate 104 for presenting the magnetic particulates 102 two-dimensionally, and an adhesive layer 105 for immobilizing the magnetic particulates 102 is present on the surface of the supporting substrate 104. As a supporting substrate 104, a thin quartz glass substrate or a thin silicon substrate which transmits the magnetic force well is suitable; according to a type of the adhesive layer 105, a quartz glass substrate deposited with a metal thin film or a silicon substrate may be used selectively. Since the magnetic particulates 102 modified with protein are well adsorbed on a hydrophobic layer, the adhesive layer 105 is formed by immobilizing an alkyl group to the surface of the supporting substrate 104. The alkyl chain with a functional group can be used as an adhesive agent. As to the functional group, a silanol group is used if the material of the supporting substrate 104 is quartz or an oxidized silicon substrate, a thiol group is used if the material is a gold-deposited substrate, and a phosphate group is used if the material is a titanium-oxide-deposited substrate. When the reaction is carried out, the functional group is immobilized to the supporting substrate, and the alkyl chains crowd with the alkyl-chain hydrophobic interaction and form a self-assembled membrane (SAM) on the surface of the supporting substrate 104. By this method, the surface of the supporting substrate 104 can be made hydrophobic uniformly. A magnetic field generator 106 for attracting the magnetic particulates 102 to the adhesive layer 105 has been installed just below the supporting substrate 104. Further, the magnetic field generator 106 is equipped with a function for switching the on/off or the intensity levels of the magnetic field. This device is used as being installing on a movable stage 107 so as to be able to scan the entire surface of the supporting substrate 104.

Hereunder, the role of the device and the observation procedure are explained. At the beginning, the reaction solution A is placed on the supporting substrate 104 using a pipette 108. By making side walls surrounding the supporting substrate 104 all around, the amount of solution per area of the supporting substrate can be adjusted strictly, and a uniform liquid thickness can be obtained as compared with a method of placing a droplet directly as is. Namely, a uniform immobilization of the magnetic particulates 102 can be achieved. In the state that the magnetic field generator 106 is turned on, because the magnetic particulates 102 are attracted from a spot where they are introduced, the magnetic particulates will be immobilized non-uniformly. Therefore, the magnetic field generator 106 is turned off when the reaction solution A is introduced, and after introduction, the magnetic field is generated by turning on the magnetic field generator 106 to attract all of the magnetic particulates 102 in the reaction solution A onto the support base 104. The magnetic particulates 102 contacting with the adhesive layer 105 are immobilized to the supporting substrate 104. Since the antibody-bound magnetic particulates 102 used in this study are paramagnet, they can be magnetized by applying a magnetic field from the outside. However, if each magnetic particulate 102 is magnetized, the magnetic particulates attract each other and form an aggregate like a string of beads. Therefore, if the observation is performed in a state that the magnetic field is applied from the outside, since the magnetic particulates 102 have a steric structure toward the direction perpendicular to the supporting substrate 104, focusing becomes difficult on observation or, by enfolding the fluorescence-labeled antibody 103 inside the aggregate, excitation light becomes non-uniform and the original quantitative performance is impaired. Therefore, by turning off the magnetic field to resolve aggregation of magnetic particulates 102, only the magnetic particulate 102 immobilized to the adhesive layer 105 is presented on the supporting substrate 104 and a magnetic particulate layer of a single layer can be formed. In this case, the magnetic particulates which did not contact with the adhesive layer 105 are not presented on the supporting substrate 104; however, if the collision chance is increased by repeating the on/off or the up-and-down of the magnetic field, most magnetic particulates 102 can be immobilized to the adhesive layer 105. After immobilizing the magnetic particulates 102 to the adhesive layer 105, all floating unreacted fluorescence-labeled antibodies 103 can be washed away by flushing the cleaning solution. In this regard, however, removal of the unreacted fluorescence-labeled antibodies 103 may be carried out in the reaction vessel 110 in advance. A photograph is taken while irradiating excitation light to the magnetic particulates 102 immobilized in a single layer on the supporting substrate 104 and the fluorescence-labeled antigens 101 bound thereto. The antigen concentration can be determined by counting the number of observed bright spots.

Example 2

Figure 2:
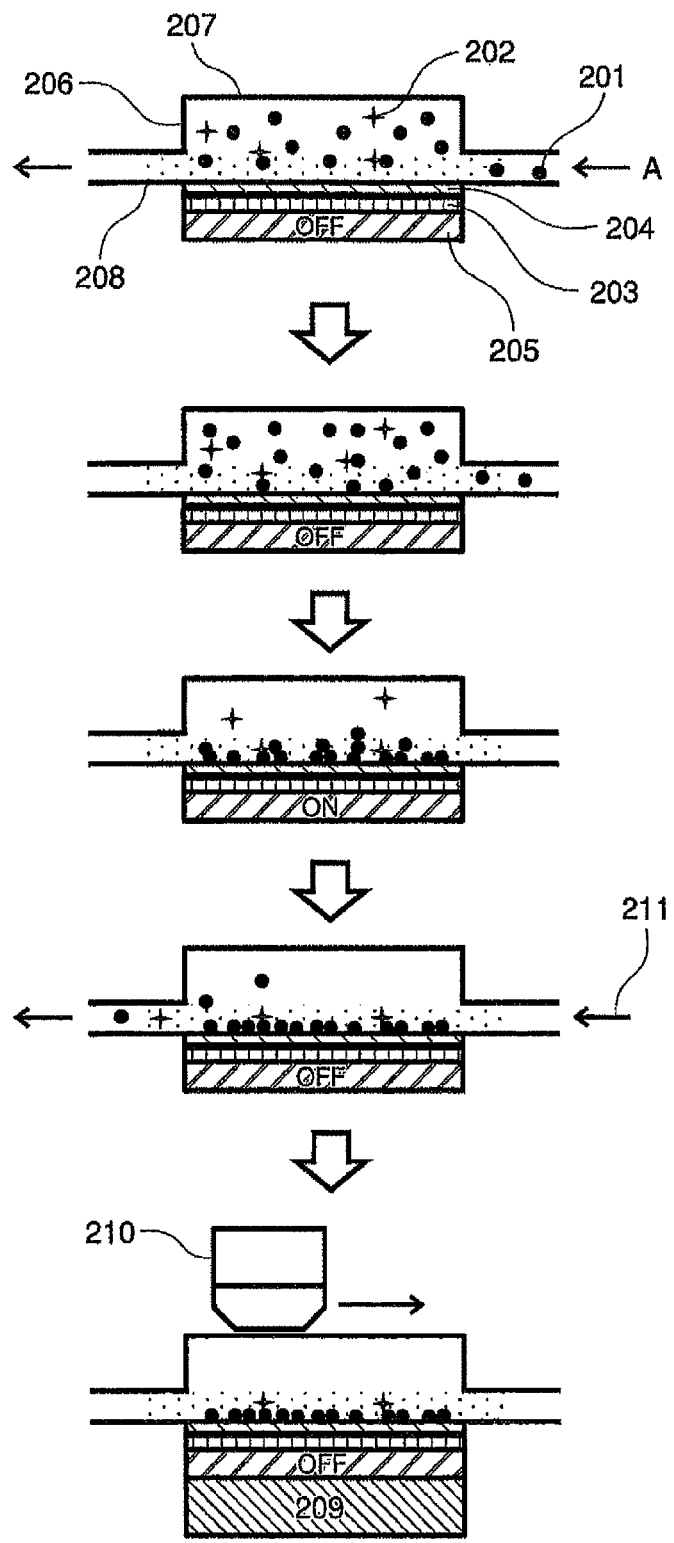
FIG. 2 is a figure for explaining one example of the configuration of the device to be used in the analysis method of the present example.

Next, a configuration of a device for fluorescence detection in combination with a flow channel is explained with reference to FIG. 2. In the same manner as in Example 1, the present device has a smooth supporting substrate 203 for presenting magnetic particulates 201 in two-dimension, and an adhesive layer 204 for immobilizing the magnetic particulates 201 on the surface of the supporting substrate 203 and a magnetic field generator 205 which is capable of switching the on/off or the intensity levels of the magnetic field for attracting the magnetic particulates 201 to the adhesive layer 204 just below the supporting substrate 203 are installed. Further, in all the directions of the supporting substrate 203, side walls 206 are installed, and further covered thereon with a smooth transparent cover member 207. For example, PDMS (polydimethylsiloxane) may be used as the material of the side wall 206, and the quartz can be used for the material of the cover member 207. Tubes 208 for inserting and removing the solution are mounted at two places of the side wall. Silicone rubber can be used as the material of the tubes 208. The magnetic field generator 205 for attracting the magnetic particulates 201 to the adhesive layer 204 is installed just below the supporting substrate 203. The present device is used as installed on a movable stage 209 so as to be able to scan the entire surface of the supporting substrate 203. Alternatively, the scanning is performed by adding a moving mechanism to a side with an objective lens 210.

Hereunder, the role of the device and the observation procedure are explained. At the beginning, a certain amount of the reaction solution A is placed in the state that the magnetic field is off. Then by generating the magnetic field, the magnetic particulates 201 in the reaction solution A are attracted onto the supporting substrate 203. The magnetic particulates 201 contacted with the adhesive layer 204 are immobilized to the supporting substrate 203. After immobilizing the magnetic particulates 201 to the adhesive layer 204, all floating unreacted fluorescent dyes 202 can be washed away by flushing a cleaning solution 211. A photograph is taken while irradiating excitation light to the magnetic particulates 201 immobilized in a single layer on the supporting substrate 203 and the fluorescent dyes 202 bound thereto. The concentration of the biomolecules can be determined by counting the number of observed bright spots.

Example 3

Figure 3:
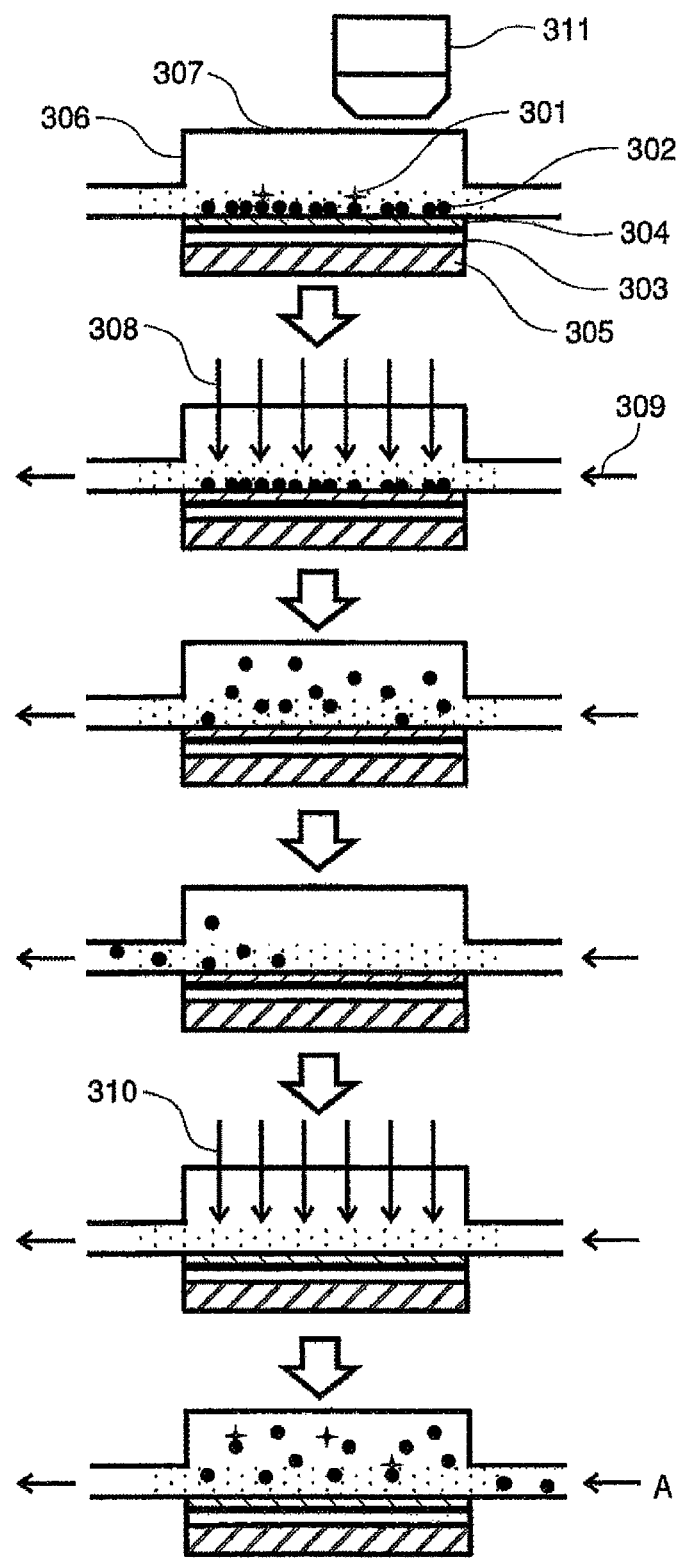
FIG. 3 is a figure for explaining one example of the configuration of the device to be used in the analysis method of the present example.

Next, a configuration of a device having a function of changing reversibly the adhesive force of an adhesive layer 304 is explained with reference to FIG. 3. In the same manner as in Example 2, the present device has a smooth supporting substrate 303 for presenting magnetic particulates 302 in two-dimension, and the adhesive layer 304 for immobilizing the magnetic particulates 302 on the surface of the supporting substrate 303 and a magnetic field generator 305 which is capable of switching the on/off or the intensity levels of the magnetic field to attract the magnetic particulates 302 to the adhesive layer 304 just below the supporting substrate 303 are installed. Further, in all the directions of the supporting substrate 303, side walls 306 are installed, and further covered thereon with a smooth transparent cover member 307. Tubes for inserting and removing a solution are mounted at two places of the side walls 306. The magnetic field generator 305 for attracting the magnetic particulates 302 to the adhesive layer 304 is installed just below the supporting substrate 303. Furthermore, the adhesive layer 304 is formed with a material which can change reversibly its adhesive force. For example, a substance which changes wettability of the surface from hydrophobic to hydrophilic or from hydrophilic to hydrophobic with use of temperature or heat is used as an adhesive agent. By changing reversibly the adhesion force of the adhesive layer 304, after observation, the supporting substrate 303 can be washed after peeling off the magnetic particulates 302 from the supporting substrate 303 immobilizing thereon the magnetic particulates 302, and further by recovering the adhesion force again, a new sample can be observed. Namely, the supporting substrate 303 is reused many times. As to the adhesive agent which achieves reuse, a photoresponsive alkyl azobenzene can be used. The azobenzene has a structure in which two benzene rings are attached to two azo groups and is isomerized to the cis form when irradiated with ultraviolet light 308 and isomerized to the more stable trans form by applying visible light 310 or heat. For example, an alkyl azobenzene with a functional group, in which an azobenzene and a functional group that reacts with the substrate side are bound to one end and the other of the alkyl chain, respectively, is prepared. The functional group to be used is a silanol group if the substrate is quartz or an oxidized silicon substrate, a thiol group if the substrate is a gold-deposited substrate, and a phosphate group if the substrate is a titanium-oxide-deposited substrate. When the reaction is performed, the functional group is immobilized to the supporting substrate and the alkyl chains crowd with the alkyl-chain hydrophobic interaction to form a self-assembled membrane (SAM) on the surface of the supporting substrate. By this method, the azobenzene can be introduced uniformly on the substrate. On the occasion of immobilizing the magnetic particulates 302, the azobenzene should be in the cis form by irradiation for approximately 5 minutes with the ultraviolet light 308.

Hereunder, the role of the device and the observation procedure is explained. At the beginning, a certain amount of the reaction solution A is placed with the magnetic field off. Then, by generating a magnetic field, the magnetic particulates 302 in the reaction solution A are attracted onto the support base. The magnetic particulates 302 contacting with the adhesive layer 304 are immobilized on the supporting substrate 303. After immobilizing the magnetic particulates 302 to the adhesive layer 304, all floating unreacted fluorescence-labeled antibodies can be washed away by flushing a cleaning solution 309. A photograph is taken while irradiating excitation light to the magnetic particulates 302 which have been immobilized onto the supporting substrate 203 in a single layer and the fluorescence-labeled antigens bound thereto. The antigen concentration can be determined by counting the number of observed bright spots.

After completion of observation, by applying visible light 310 or heat to a supporting substrate 303 on which the magnetic particulates 302 have been immobilized, the azobenzene is made hydrophilic, and the magnetic particulates 302 are peeled off from the supporting substrate 303. Irradiation of visible light 310 is set to be able to irradiate the entire surface of the supporting substrate 303 by preparing a light source and a wavelength separation filter aside from the detection system. In order to apply heat, hot water heated to 35° C. or higher is passed through the flow channel. In either method of making hydrophilic, higher removing effect of the magnetic particulates 302 than that obtained by washing with an aqueous solution containing a surface active agent can be obtained. When cleaning has completed, the azobenzene is returned to the cis form again by irradiation with the ultraviolet light 308 for approximately 5 minutes, and immobilization and observation are carried out in the same way by placing a new sample.

When immobilizing and removing are carried out repeatedly in this way, there is a possibility that fluorescent dyes 301 immobilized in the previous time may remain, and would be added in on the second and/or subsequent quantification. In order to prevent this, washing conditions with which the magnetic particulates 302 can be removed completely or until down to an acceptable amount are determined in advance. When a trace of sample is quantified, a difference of a few bright spots may affect quantitative results significantly. At that time, it is possible to completely remove contaminations by changing the wavelength of the fluorescent dyes 301 to be used for labeling and the detection filter in each of measurement times.

Example 4

Figure 4:
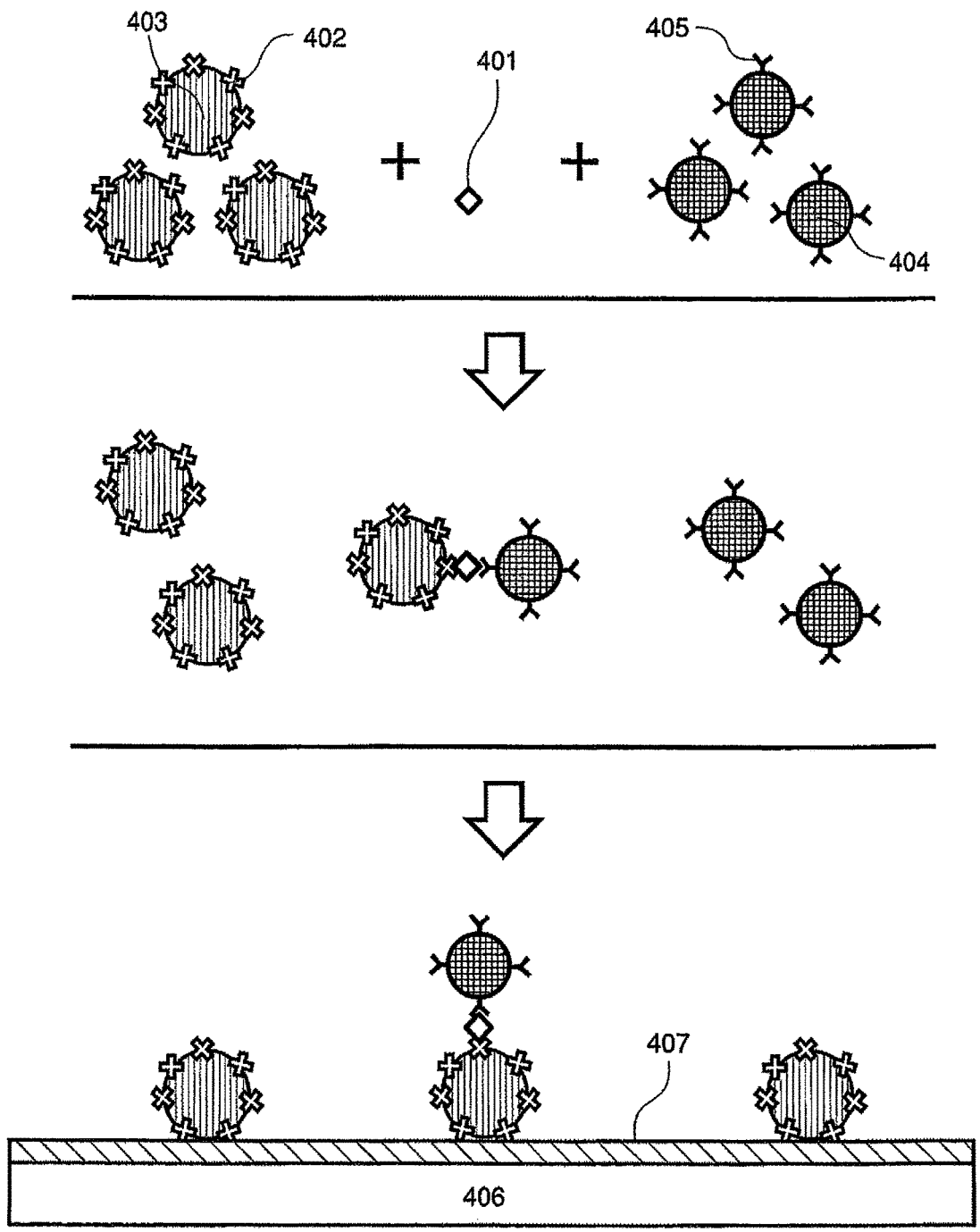
FIG. 4 is a figure for explaining one example of a method for capturing the antigenic molecules and a method for fluorescence-labeling the antigenic molecules in the present example.

A sample preparation method in the present Example is explained with reference to FIG. 4. When biomolecules to be detected are antigens 401, they are captured in advance by magnetic particulates 403 bound to antibodies 402, and further labeled with fluorescence-labeled antibodies 405. All of these reactions are carried out in a buffer for reaction (Tris buffer (pH 8.0), 50 mM NaCl, 0.1% Tween 20) under a normal temperature. Either one of the reaction between the particulate bound to the antibody 402 and the antigen 401 and the reaction between the fluorescence-labeled antibody 405 and the antigen 401 may be carried out first, or they may be carried out at the same time. Any kind can be used as an antigen 401; however, as an antibody 402, it is preferable to select one with high specifity against the antigen 401. For example, when PSA (prostate specific antigen) which is a tumor marker for prostate cancer is selected as an antigen 401, a PSA antibody is required. For the PSA antibody, one for binding with a magnetic particulate and another for being labeled with a fluorescent dye are required respectively. The antibodies may be either a polyclonal antibody or a monoclonal antibody, and are selected appropriately according to the type of the antigen 401.

When the antibodies 402 are bound to the magnetic particulates 403, Protein A modified or Protein G modified magnetic particulates 403 which can bind with the antibody 402 while maintaining the activity of the antibody 402 is prepared. Such magnetic particulates 403 are commercially available and can be easily obtained. For example, Protein A modified Adembeads which are paramagnetic particulates (φ300 nm) from Ademtech Inc. can be used. The Protein A modified magnetic particulates 403 are mixed with about 10 times or more of PSA antibodies and incubated. Then, after the magnetic particulates 403 are captured with a magnet, the solution is removed, and they are suspended in a clean buffer. This operation is repeated until the unreacted antibodies 402 are removed. The magnetic particulates 403 modified with streptavidin can be used as the magnetic particulates 403. For example, streptavidin-modified Adembeads (φ100 nm, φ200 nm, φ300 nm) from Ademtech Inc. can be used. When these magnetic particulates 403 are used, the antibodies 402 are bound to the surfaces of the magnetic particulates 403 by using biotinylated antibodies 402. The diameter of the magnetic particulates 403 to be used is desirably selected from those which are smaller than the excitation wavelength, thereby an increase in background due to scattered light of the magnetic particulates 403 can be prevented.

Various types of fluorescence-labeled antibodies are commercially available. For example, FITC, Alexa®, CY5, and the like are well known. However, in the present study, in order to enable detection of the antigen 401 of at least one molecule, it is desirable to use a fluorescent dye with high brightness and a long quenching time. As such a fluorescent dye, for example, a dendrimer-type fluorescent dye, in which fluorescent dyes of several hundred molecules are bonded to one branched carbon chain, or a quantum dot 404 can be used.

In the present Example, a fluorescence labeling method of antibodies using quantum dots 404 is explained. The quantum dots 404 are the semiconductor fine particulates with a diameter of a few nanometers to several tens of nanometers. They have a long lifetime and high brightness as compared to the conventional fluorescent dyes, and emit fluorescence of different wavelengths according to the particle sizes. Quantum dots 404 are commercially available from several manufacturers, and some are modified with various functional groups. As the quantum dots 404 that can bind any fluorescence-labeled antibodies 405, for example, Qdot® antibody labeling kit from Invitrogen Corporation can be utilized. In this kit, the quantum dots 404 introduced with a thiol group on the surface and the fluorescence-labeled antibodies 405 with the disulfide bond reduced are mixed and reacted, thereby the fluorescence-labeled antibodies 405 can be labeled with the quantum dots 404.

Using the magnetic particulates 403 bound to antibodies 402, which are prepared as described above, and the fluorescence-labeled antibodies 405, capture and detection of antigens 401 are carried out. First, the magnetic particulates 403 bound to antibodies 402 are placed in the reaction vessel and stirred well. To this solution, a solution containing the antigens 401 to be detected is added and mixed well; then it is incubated for 1 hour. At this time, the reactions between the antigens 401 and the antibodies 402 are accelerated by either rotating the vessel up and down or by agitating with shaking. As to the ratio of mixing, the magnetic particulates 403 bound to antibodies 402 are mixed with the antigens 401 so as to be excessive as compared with the antigens 401. Specifically, to an assumed amount of the antigens, 100 to 10,000 times the amount of the magnetic particulates 403 bound to antibodies 402 is placed. Then, to this reaction solution, the fluorescence-labeled antibodies are placed, and it is incubated for an additional few minutes. The fluorescence-labeled antibodies 405 are also placed to be a 100 to 10,000 times more amount so as to be in excess of the amount of the antigens. By placing each in an excessive amount, collision frequencies with the antigens 401 increase and the capture rate and the fluorescence labeling index of the antigens 401 can be improved. The mixture reacted as described above is observed in the same manner as in the reaction solution of Example 3 and the antigens 401 are determined quantitatively.

Example 5

Figure 5:
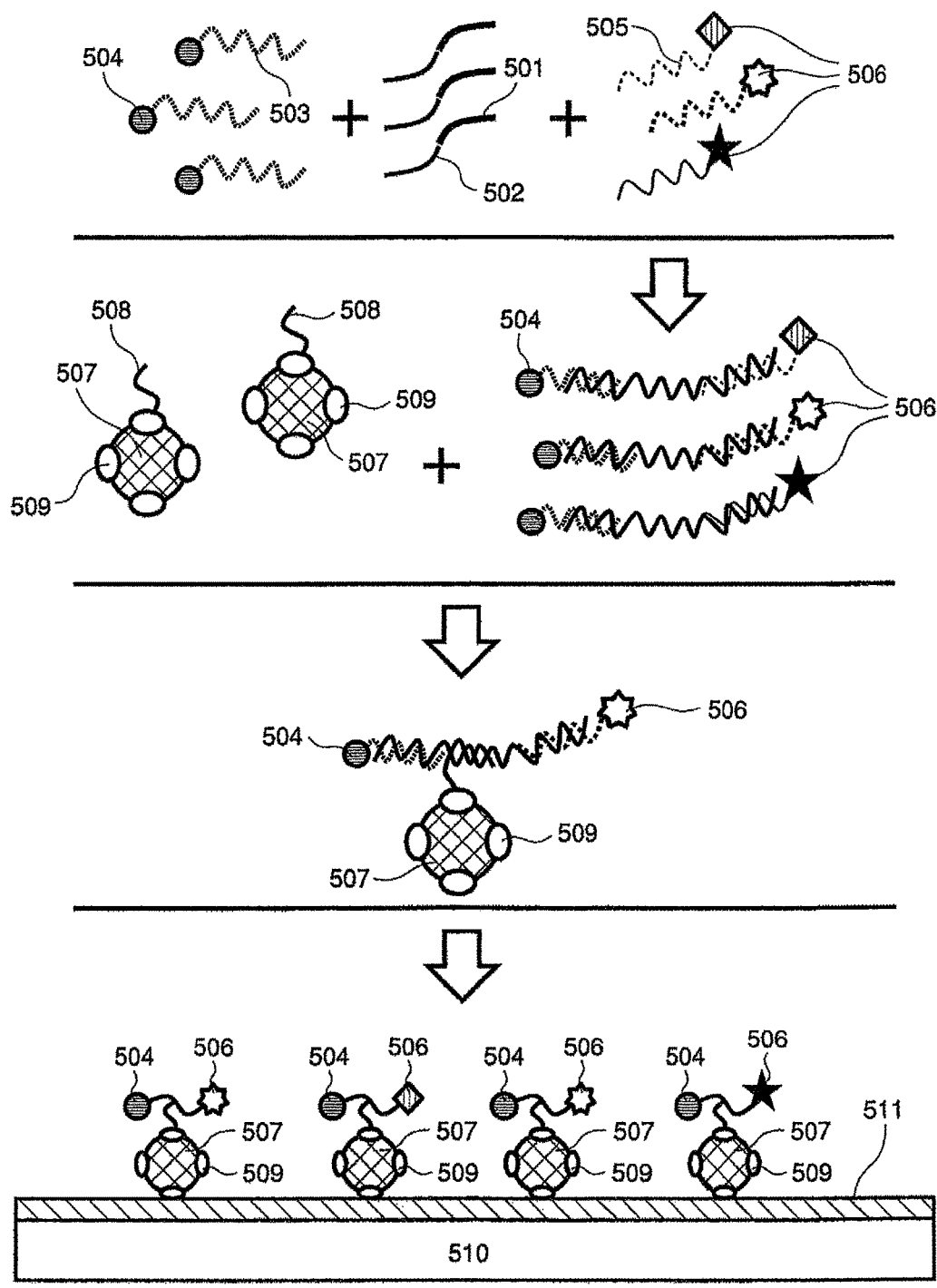
FIG. 5 is a figure for explaining one example of a method for capturing the nucleic acid fragments and a method for fluorescence-labeling the nucleic acid fragments in the present example.

The sample preparation method in the present study is explained with reference to FIG. 5. When biomolecules to be detected are nucleic acid fragments, sample nucleic acid fragments 501 of the detection objects are captured by magnetic particulates 507, and further labeled with nucleic acid fragments 505 bound to fluorescent dyes 506 having sequences complementary to the sample nucleic acid fragments 501. This is a specific reaction by hybridization, and is carried out in a buffer for reaction (PBS buffer (pH 7.4), 50 mM to 1 M NaCl, 0.1% Tween 20). Either one of the reaction between the magnetic particulate 507 attached with nucleic acid and the sample nucleic acid fragment 501 and the reaction between the nucleic acid fragment 505 attached with the fluorescent dye 506 and the sample nucleic acid fragment 501 may be carried out first, or they may be carried out at the same time. For the nucleic acid fragments 505, single-stranded DNAs or single-stranded RNAs can be used. Details are explained while taking a micro-RNA as an example of a concrete analysis object.

A micro-RNA is a single-stranded nucleic acid fragment of about 20 mer. The simplest detection method is a method of direct fluorescence labeling of the sample nucleic acid fragment 501. In this case, a biotinylated sample nucleic acid fragment 501 is prepared by binding a biotinylated dUTP to the 3' terminal side of the sample nucleic acid fragment 501. An avidin-labeled quantum dot is reacted to this sample nucleic acid fragment 501. In the same way, a magnetic particulate 507 attached with a complementary strand to the sample nucleic acid fragment 501 is prepared, and allowed to react with the sample nucleic acid fragment 501 which has been reacted with the quantum dot. The amount of the sample nucleic acid fragments 501 captured by the magnetic particulates 507 is measured from the fluorescent dyes 504.

When the amount of specific micro-RNAs among the total amount of overall micro-RNAs is to be measured, nucleic acid fragments each of which contains a consensus sequence 503 and a capture sequence 508 should be added to the ends of the micro-RNAs of the sample nucleic acid fragments 501 by ligation in advance. The consensus sequence 503 refers to a sequence for fluorescence-labeling of all micro-RNA irrespective of the type, and the capture sequence refers to a sequence for being captured by magnetic particulates 507. As to the consensus sequence and the capture sequence, a GC content and a base length can be synthesized arbitrarily in accordance with the Tm value of the sample to be measured. Hereinafter, the nucleic acid fragment containing a consensus sequence and a capture sequence is referred to as a tag fragment 502. First, a complementary strand to the consensus sequence labeled with a fluorescent dye 504 and a complementary strand to a sample nucleic acid fragment 501 labeled with a fluorescent dye 506 are prepared. These are mixed and hybridized with the sample nucleic acid fragment 501 added with a tag molecule 502. At this time, when plural types of sample nucleic acid fragments 501 are present, the strands complementary to sample nucleic acid fragments 501 are prepared for respective types, and labeled with fluorescent labels of different wavelengths, respectively. The sample nucleic acid fragments 501 fluorescence-labeled in this way are captured with magnetic particulates 507 bound with the capture sequence. This reaction is also performed by hybridization. The magnetic particulates 507 capturing the fluorescence-labeled sample nucleic acid fragments 501 are immobilized to the adhesion layer on the supporting substrate, and observation of the bright spots is performed in the same manner as in Examples 1 and 2. At this time, the number of fluorescent bright spots of the consensus sequence side corresponds to the total number of micro-RNAs, and the number of fluorescent bright spots of the sample side corresponds to the number of molecules of the sample nucleic acid fragments 501. Judging the ratio of the numbers of both the bright spots as the abundance ratio of each type of the nucleic acid sample molecules is also effective when the expression level of only a particular nucleic acid molecule is desired to be examined.

The magnetic particulates 507 are commercially available and can be obtained easily. For example, streptavidin-modified magnetic particulates from Ademtech Inc., which are paramagnetic particulates, can be used. For example, streptavidin-modified Adembeads ($\varphi$100 nm, $\varphi$200 nm, $\varphi$300 nm) from Ademtech Inc. can be used. When these magnetic particulates are used, the nucleic acids are bound to avidin 509 on the surface of the magnetic particulates 507 using a biotinylated nucleic acid fragments. The diameter of the magnetic particulates 507 to be used is desirably selected from those which are smaller than the excitation wavelength, thereby an increase in background due to scattered light of the magnetic particulates 507 can be prevented. Various types of fluorescent dyes are commercially available. For example, FITC, Alexa®, and CY5 are well known. However, in the present study, in order to enable detection of the sample nucleic acid fragments of at least one molecule, it is desirable to use a fluorescent dye with high brightness and a long quenching time. As such a fluorescent dye, for example, a dendrimer-type fluorescent dye, in which fluorescent dyes of several hundred molecules are bonded to one branched carbon chain, or a quantum dot 404 can be used. In the present Example, a fluorescence labeling method of nucleic acid fragments using quantum dots is explained. For example, streptavidin-modified Qdot® from Invitrogen is available. Bindings between the quantum dots and the nucleic acid fragments may be performed by mixing and followed by incubation for more than 30 minutes, and after reaction unreacted nucleic acid fragments are removed with a spin column of 50 kDa cut-off.

Using the magnetic particulates 507 bound with the capture sequence and a fluorescent dye-labeled nucleic acid fragments labeled by fluorescent dyes that are prepared as described above, the sample nucleic acid fragments 501 are captured. First, the magnetic particulates 507 bound with the capture sequence are placed in a reaction vessel and stirred well. To this solution, a solution containing the sample nucleic acid fragments 501 to be detected is added, mixed well, and then incubated for 6 hours. At this time, the hybridization reaction is accelerated by either rotating the reaction vessel up and down or by agitating with shaking. As to the ratio of mixing, the magnetic particulates 507 are mixed with the nucleic acid fragments so as to be excessive as compared with the objective nucleic acid fragments.

Specifically, to an assumed number of the sample molecules, 100 to 10,000 times the amount of the magnetic particulates 507 are placed. The reaction solution treated as described above is observed in the same manner as in Examples 1 and 2.

Example 6

Figure 6:
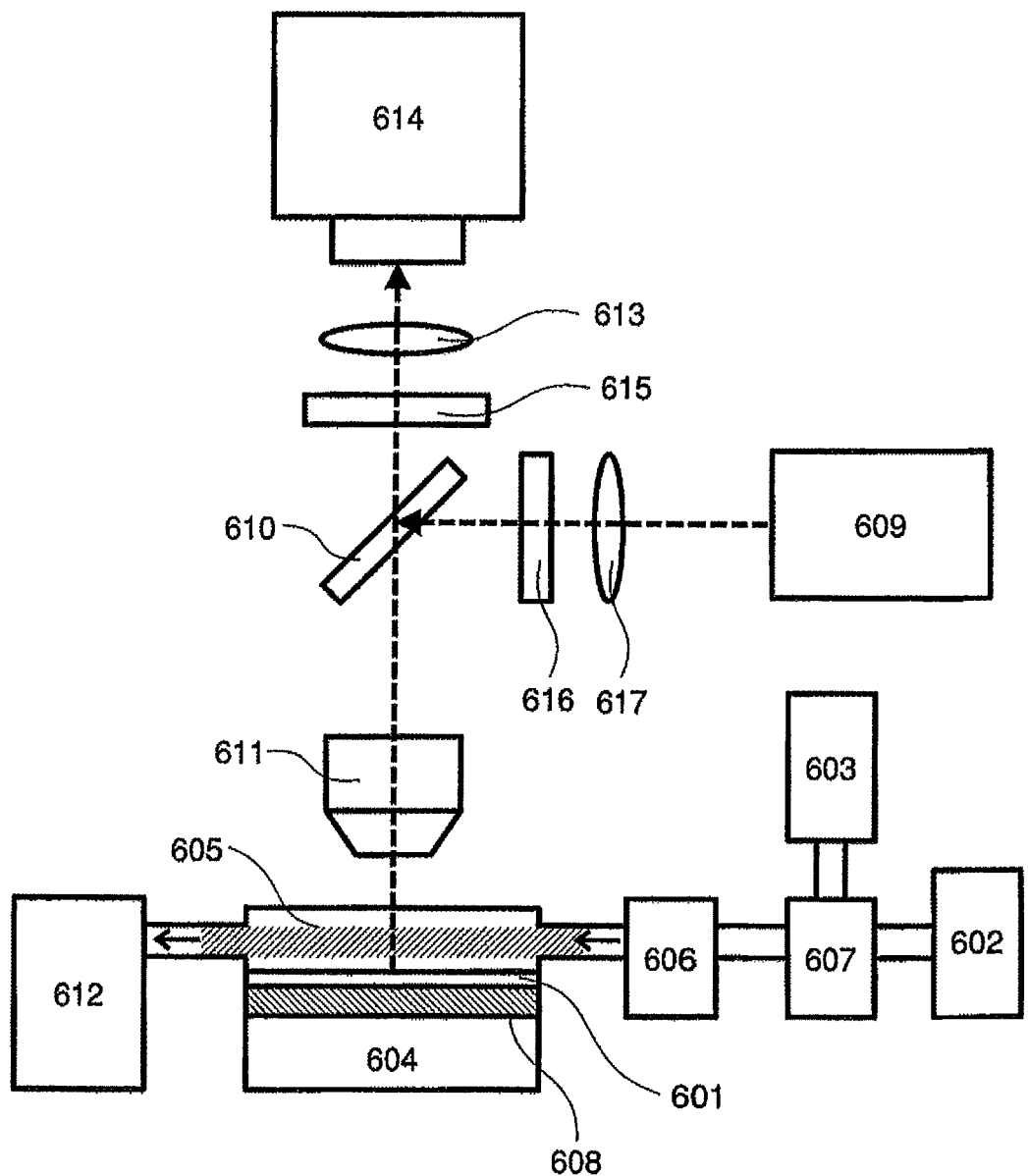
FIG. 6 is a figure for explaining one example of the configuration of a biomolecule analyzer of the present example.

In the present Example, one example of a preferred configuration of the biomolecule analyzer is explained with reference to FIG. 6. The biomolecule analyzer of the present Example is equipped with a means for supplying the biomolecule solution of the analysis object and the cleaning solution to a supporting substrate 601 for deploying the biomolecules two-dimensionally, a means for attracting the magnetic particulates on the supporting substrate, a means for holding the magnetic particulates on the supporting substrate, a means for controlling the temperature for heating the cleaning solution in the supporting substrate, a means for irradiating the light to the supporting substrate, an emission detection means for measuring the fluorescence of the phosphor of the fluorescence-labeled molecule, and a means for scanning the supporting substrate 601.

More specifically, by placing the supporting substrate 601 on a movable stage 604 and sticking the flow path member provided with the flow channel together thereon, a reaction chamber 605 is formed. As to the flow path member, for example, PDMS (polydimethylsiloxane) can be used. A liquid feed pump 607 is connected at an inlet 606, and the biological sample solution and the cleaning solution are supplied sequentially to the supporting substrate 601 from a solution tank 602 of the biological sample of the analysis object and a cleaning solution tank 603, and discarded to a waste liquid tank 612 after use. Once the biological sample solution enters the reaction chamber, a magnetic field generator 608 generates a magnetic field to attract the magnetic particulates onto the surface of the supporting substrate 601. The attracted magnetic particulates contact with the adhesive layer on the surface of supporting substrate and are immobilized. Washing is carried out by introducing the cleaning solution into the reaction chamber 605 from the liquid feed pump 607. After washing, fluorescence detection is carried out. An excitation light source 609 can be selected appropriately according to a type of a phosphor to be used. For example, in the case where the quantum dots are used as a fluorescent dye for fluorescent labeling, the light source can be accommodated with 532 nm (YAG laser) or a mercury lamp. The excitation light emitted from the excitation light source 609 is passed through an excitation filter 616 and a lens 617, is led to an objective lens 611 by a dichroic mirror 610, and irradiates onto the supporting substrate 601. The fluorescent light emitted from fluorescence-labeled molecules on the support base 601 travels on the same light path as the excitation light in an opposite direction, passes through the dichroic mirror 610 after collected by the objective lens 611, and is imaged on a photosurface of a two-dimensional CCD camera 614 by an imaging lens 613. Scattered light of the excitation light is removed by an absorption filter 615. In order to improve quantitative performance, it is necessary to increase the number of bright spots for observation. The bright spots can be increased by operating the movable stage 604 so that the entire surface of the supporting substrate 601 is scanned. By assembling a biomolecule analyzer with the liquid feed pump 607, the inlet 606, the excitation light source 609 and the fluorescence detection unit, the magnetic field generator 608, and the movable stage 604 as described above, automatic analysis can be performed and thereby speed improvement can be achieved.

Example 7

Figure 7:
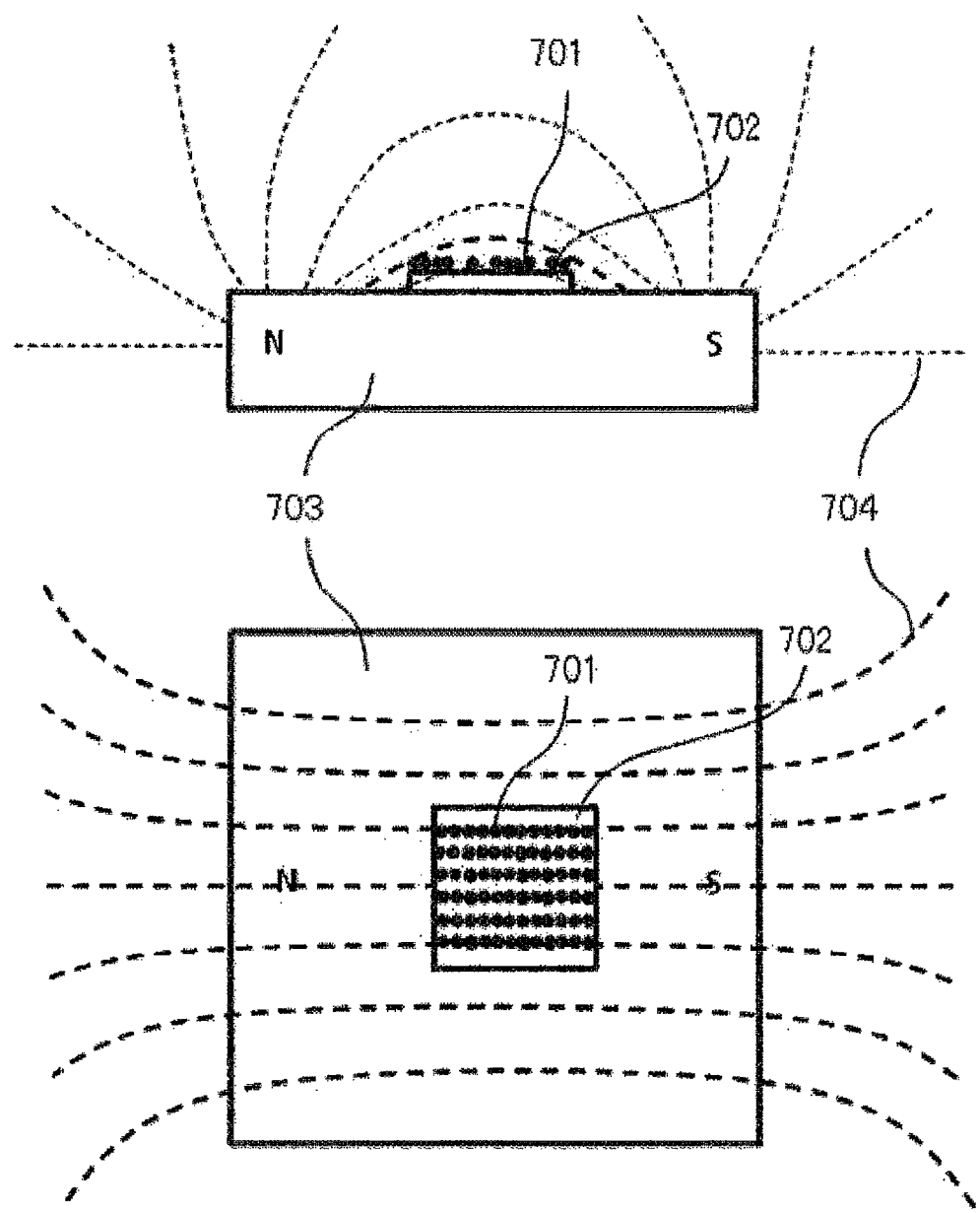
FIG. 7 is a figure for explaining one example of a method for immobilizing the magnetic particulates using a magnet, in the present example.

In the present Example, with regard to an arrangement of a magnet and a supporting substrate to be used for immobilizing magnetic particulates 701, one of the configurations that are desirable to be used in combination with Examples 1 to 5 is explained with reference to FIG. 7. Since the equipment to be used in the present invention scans the surface of a smooth supporting substrate 702, the more magnetic particulates 701 which are immobilized to a unit area, the more advantageous it is in terms of throughput. On the other hand, if there too many magnetic particulates 701 per area, they are multi-layered and the magnetic particulates 701 that do not fit within the depth of focus of the objective lens increase so that the number of detection decreases. Therefore, in order to implement an efficient detection, it is desirable that the magnetic particulates 701 are to form a thin layer while being immobilized at high density. Accordingly, a method for immobilizing the magnetic particulates 701 with use of a powerful magnet 703 having magnetic field lines 704 parallel to the supporting substrate 702 was devised.

Figure 8:
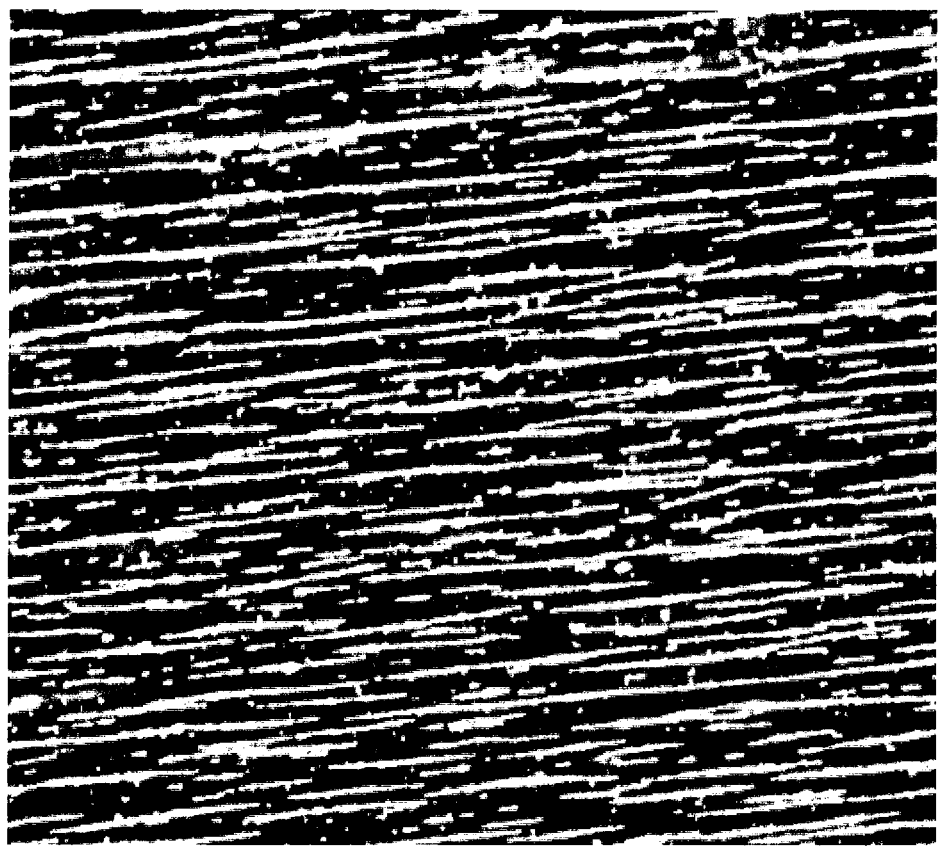
FIG. 8 is a microscopic image of the magnetic particulates immobilized using a magnet, in the present example.

The arrangement method follows. As shown in FIG. 7, at first, the magnetic particulates 701 were put on the supporting substrate 702; then, the supporting substrate 702 was arranged on the magnetic field generator 703. The directions and the intensities of the magnetic field lines 704 had been examined in advance and the supporting substrate 702 was arranged so that the directions of the magnetic field lines 704 in the central part of the surface of the supporting substrate 702 were parallel. Further, by performing the immobilizing reaction for a few seconds, the magnetic particulates 701 could be immobilized in a form of lines as shown in FIG. 8. As a result of extensive studies on positions of the above arrangement, it turned out that, by arranging the supporting substrate 702 on the surface of the magnet 703 and also at a central part as much as possible between both poles, using the magnet 703 larger than the supporting substrate 702, and further using the magnet 703 having high magnetic flux densities, more uniform and quicker immobilization can be achieved.

The principle of immobilization follows. The normal magnet forms magnetic field lines 704 which draw arcs between both poles. At that time, in the central part of the surface of the magnet 703 belt-shaped magnetic field lines 704 that connect in parallel between both poles are formed. Since the magnetic particulates 701 used in the present Example have a paramagnetic property, by applying a magnetic field from the outside, each particulate was magnetized and formed a bead-like linear chain with other magnetic particulates 701 according to the parallel magnetic field lines 704 (FIG. 8). In this occasion, the parallel magnetic force generated in the center of the magnet 703 is very weak compared to the magnetic force that arises at the both poles. Therefore, it is desirable that the arranged magnetic particulates 701 are placed with sufficient distances from the poles so as not to be pulled toward either pole. Namely, it is desirable to be located in the central part between the both poles, and a bias of immobilization can be reduced by placing with sufficient distances. The term "sufficient" mentioned here can be achieved, for example, by making the distance from the center of the supporting substrate 702 which is a 4-mm square to each pole be 40 mm. In addition, the parallel magnetic field generated in the center of the magnet 703 requires a magnetic force component perpendicular to the magnet 703 for immobilizing the magnetic particulates 701 on the supporting substrate 702. Therefore, it is possible to increase the immobilization rate by choosing the magnet 703 with a relatively strong magnetic force. This is also advantageous in that the magnetic particulates 701 are immobilized at a high density; specifically, a surface magnetic flux density of 0.1 T or higher is desirable. In the present Example, a neodymium magnet of 0.5 T in φ8 cm and a supporting substrate 702 of a 4-mm square were used. When the magnetic particulates are attracted in the vicinity of the poles of the magnet 703, chains of the magnetic particulates would extend in a direction perpendicular to the supporting substrate. In fact, when the equal amount (20 pM) of the magnetic particulates 701 (φ300 nm) is introduced in the same volume (4×4×0.13 mm) and a parallel magnetic flux and a perpendicular magnetic flux are applied with respect to the supporting substrate 702, respectively, the magnetic particulate density that fits within the same depth of focus on the surface of the supporting substrate 702 was about 8 times higher in the parallel magnetic flux. Hereby, it could be confirmed that the parallel magnetic flux was effective in high-density immobilization of the magnetic particulates.

REFERENCE SIGNS LIST

101, 401 antigen
102, 201, 302, 403, 507 magnetic particulate
103, 405 fluorescence-labeled antibody
104, 203, 303, 406, 601 supporting substrate
105, 204, 304, 407, 511 adhesive layer
106, 205, 305, 608 magnetic field generator
107, 209, 604 movable stage
108 pipette
109, 210, 611 objective lens
110 reaction vessel
202, 301, 504, 506 fluorescent dye
206, 306 side wall
207, 307 cover material
208 tube
211, 309 cleaning solution
308 ultraviolet light
310 visible light
311 capturing molecule
402 antibody
404 quantum dot
501 sample nucleic acid fragment
502 tag molecule
503 consensus sequence
505 nucleic acid fragment
508 capture sequence
509 avidin
510 support base
602 biological sample solution tank
603 cleaning solution tank
605 reaction chamber
606 inlet
607 liquid feed pump
609 excitation light source
610 dichroic mirror
612 waste liquid tank
613 imaging lens
614 two-dimensional CCD camera
615 absorption filter
616 excitation filter
617 lens
701 magnetic particulate
702 supporting substrate
703 magnet
704 magnetic field line (magnetic flux)

The invention claimed is:

1. An analysis device to quantitatively measure biological molecules using a fluorescent dye, comprising:
   a support base having an upper surface with a length on which an adhesive layer is continuously disposed across an entirety of the length, the adhesive layer is a photoresponsive alkyl azobenzene with a functional group, and the adhesive layer is configured to adhere magnetic particulates across the entirety of the length which capture the biological molecules and the fluorescent dye on the adhesive layer;
   a magnetic field generator disposed adjacent to the support base and which is configured to turn on to generate a magnetic field to attract the magnetic particulates toward the adhesive layer and switch to reduce or turn off the magnetic field so that a single layer of the magnetic particulates is adhered to the adhesive layer and the biological molecules and the fluorescent dye are captured by the single layer of the magnetic particulates;
   an excitation light source which is configured to excite the captured fluorescent dye; and
   a fluorescence detector which is configured to detect fluorescence from the captured fluorescent dye,
   wherein the fluorescence corresponds to a quantity of the captured biological molecules.

2. The analysis device according to claim 1, further comprising:
   a movable stage which moves the support base.

3. The analysis device according to claim 1, further comprising:
   a liquid feed pump;
   an intake port connected with the liquid feed pump; and
   an exhaust port which defines a flow path across the upper surface of the support base with respect to the intake port,
   wherein the liquid feed pump is configured to pump a cleaning solution along the flow path and flush the cleaning solution over the adhesive layer from the intake port to the exhaust port to remove non-captured fluorescent dye from the adhesive layer.

4. The analysis device according to claim 1, wherein the biological molecules and the fluorescent dye are captured by the single layer of the magnetic particulates adhered across the entire length of the adhesive layer.

5. The analysis device according to claim 1, wherein the magnetic field generator includes any one of an electromagnet, a movable permanent magnet, an electromagnet combined with a movable magnetic field shield, and a permanent magnet combined with a movable magnetic field shield.

6. The analysis device according to claim 1, wherein the fluorescence detector is an epi-illumination optical microscope.

7. The analysis device according to claim 1, wherein the fluorescence detector is an epi-illumination optical microscope which identifies two or more kinds of the fluorescence simultaneously.

8. An analysis method to quantitatively measure biological molecules using a fluorescent dye, comprising:
   providing a support base having an upper surface with a length on which only an adhesive layer, which is a photoresponsive alkyl azobenzene with a functional group, is continuously disposed across an entirety of the length;

providing a solution including magnetic particulates, the biological molecules and the fluorescent dye over the adhesive layer;

generating a magnetic field to attract the magnetic particulates towards the adhesive layer and adhering the magnetic particulates to the adhesive layer, wherein the adhesive layer is configured to adhere magnetic particulates across the entirety of the length;

reducing or turning off the magnetic field so that a single layer of the magnetic particulates is adhered to the adhesive layer and the biological molecules and the fluorescent dye are captured by the single layer of the magnetic particulates;

exciting the captured fluorescent dye with a light source; and detecting fluorescence from the captured fluorescent dye, the fluorescence corresponding to a quantity of the captured biological molecules.

9. The biomolecule analysis device according to claim 1, wherein the magnetic field generator is configured to generate parallel magnetic fluxes with respect to the support base.

10. The biomolecule analysis device according to claim 1, wherein a surface magnetic flux density which the magnetic field generates in the support base is 0.1 T or higher.

11. The analysis method according to claim 8, further comprising:

flushing away non-captured fluorescent dye from the adhesive layer prior to exciting the captured fluorescent dye.

12. The analysis method according to claim 8, further comprising:

irradiating the adhesive layer with visible light having a first wavelength after detecting the fluorescence from the captured fluorescent dye; and removing the fluorescent dye, the biological molecules and the single layer of the magnetic particulates from the adhesive layer.

13. The analysis method according to claim 8, further comprising:

irradiating the adhesive layer with ultraviolet light having a second wavelength after removing the fluorescent dye, the biological molecules and the single layer of the magnetic particulates from the adhesive layer.

14. The analysis method according to claim 8, wherein the magnetic particulates have approximate diameters of 100 nm, 200 nm or 300 nm.

15. The analysis method according to claim 8, wherein the fluorescent dye is a plurality of quantum dots.

16. The analysis method according to claim 8, wherein the fluorescent dye comprises plural kinds of phosphors with different composition ratios for respective types of biomolecules to be analyzed.

17. The analysis method according to claim 8, wherein the biological molecules are antigen molecules, wherein the magnetic particulates are antibody-bound magnetic particulates, and wherein the biological molecules are captured by the single layer of the magnetic particulates through an antigen-antibody reaction.

18. The analysis method according to claim 8, wherein the biological molecules are nucleic acid molecules, and wherein the biological molecules are captured with hybridization.

19. The analysis method according to claim 8, wherein sidewalls surround the support base.

20. The analysis device according to claim 1, wherein sidewalls surround the support base.

\* \* \* \* \*